US012629664B2

(12) United States Patent
Karpov et al.

(10) Patent No.: US 12,629,664 B2
(45) Date of Patent: May 19, 2026

(54) METHOD FOR PREPARING A SILVER IMPREGNATION SOLUTION

(71) Applicant: BASF SE, Ludwigshafen am Rhein (DE)

(72) Inventors: Andrey Karpov, Ludwigshafen am Rhein (DE); Andreas Lehr, Ludwigshafen am Rhein (DE); Daniela Rieck, Ludwigshafen am Rhein (DE); Holger Borchert, Ludwigshafen am Rhein (DE); Tobias Weinland, Ludwigshafen am Rhein (DE); Marco Bosch, Ludwigshafen am Rhein (DE); Christian Walsdorff, Ludwigshafen am Rhein (DE); Christian Bartosch, Ludwigshafen am Rhein (DE); Juergen Zuehlke, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 615 days.

(21) Appl. No.: 16/968,548

(22) PCT Filed: Feb. 6, 2019

(86) PCT No.: PCT/EP2019/052918
§ 371 (c)(1),
(2) Date: Aug. 7, 2020

(87) PCT Pub. No.: WO2019/154863
PCT Pub. Date: Aug. 15, 2019

(65) Prior Publication Data
US 2021/0039074 A1    Feb. 11, 2021

(30) Foreign Application Priority Data
Feb. 7, 2018    (EP) ..................................... 18155566

(51) Int. Cl.
*B01J 23/50* (2006.01)
*B01J 35/10* (2006.01)
(Continued)

(52) U.S. Cl.
CPC ............. *B01J 23/50* (2013.01); *B01J 35/612* (2024.01); *B01J 37/0203* (2013.01);
(Continued)

(58) Field of Classification Search
CPC .... B01J 23/50; B01J 37/0203; B01J 37/0213; B01J 37/08
See application file for complete search history.

(56) References Cited

U.S. PATENT DOCUMENTS 4,007,135 A    2/1977  Hayden et al.
4,010,115 A    3/1977  Nielsen et al.
(Continued)

FOREIGN PATENT DOCUMENTS

CA    1026763 A    2/1978
CA    2783604 A1 *  7/2011   ............. C07C 11/04
(Continued)

OTHER PUBLICATIONS

Machine translation of Shima (JP2005052838), publication date Mar. 3, 2005.*
(Continued)

*Primary Examiner* — Jun Li
(74) *Attorney, Agent, or Firm* — Faegre Drinker Biddle & Reath LLP

(57)    ABSTRACT
A method for preparing a silver impregnation solution comprises (a) charging a neutralization reactor R1 with an aqueous organic amine; (b) adding oxalic acid powder through a first feeding conduit to the neutralization reactor R1 to obtain an aqueous oxalic acid-organic amine solution; (c) directing the aqueous oxalic acid-organic amine solution
(Continued)

from the neutralization reactor to a complexation reactor R2; (d) adding particulate silver oxide through a second feeding conduit to the complexation reactor R2 to obtain a silver impregnation solution; and, optionally, (e) subjecting the silver impregnation solution to filtration. The silver impregnation solution is used for producing a catalyst effective in the oxidative conversion of ethylene to ethylene oxide. The method allows for the preparation of a silver impregnation solution in an efficient and occupationally and environmentally safe way. Security hazards which can occur when oxalic acid and silver oxide are added to an aqueous amine solution using the same powder feeding equipment or the same reactor are avoided.

22 Claims, 7 Drawing Sheets

(51) Int. Cl.

| | | |
|---|---|---|
| *B01J 35/61* | (2024.01) | |
| *B01J 37/02* | (2006.01) | |
| *B01J 37/08* | (2006.01) | |
| *C07D 301/02* | (2006.01) | |
| *B01J 35/55* | (2024.01) | |

(52) U.S. Cl.

CPC ........... *B01J 37/0213* (2013.01); *B01J 37/08* (2013.01); *C07D 301/02* (2013.01); *B01J 35/55* (2024.01); *B01J 2235/00* (2024.01)

(56) References Cited

U.S. PATENT DOCUMENTS

| | | | |
|---|---|---|---|
| 4,324,699 A | 4/1982 | Mross et al. | |
| 4,356,312 A | 10/1982 | Nielsen et al. | |
| 4,690,913 A | 9/1987 | Nojiri et al. | |
| 4,728,634 A | 3/1988 | Boxhoorn et al. | |
| 4,731,350 A | 3/1988 | Boxhoorn et al. | |
| 4,732,918 A | 3/1988 | Lohmueller et al. | |
| 4,746,749 A * | 5/1988 | Nojiri ................... | C07C 51/412 |
| | | | 556/114 |
| 4,766,105 A | 8/1988 | Lauritzen | |
| 4,908,343 A | 3/1990 | Bhasin | |
| 5,100,859 A | 3/1992 | Gerdes et al. | |
| 5,187,140 A | 2/1993 | Thorsteinson et al. | |
| 5,504,052 A | 4/1996 | Rizkalla et al. | |
| 5,504,053 A | 4/1996 | Chou et al. | |
| 5,646,087 A | 7/1997 | Rizkalla et al. | |
| 5,801,259 A | 9/1998 | Kowaleski | |
| 7,553,795 B2 | 6/2009 | Bortinger et al. | |
| 7,714,152 B2 | 5/2010 | Pak | |
| 7,932,408 B2 | 4/2011 | Gückel | |
| 7,977,274 B2 | 7/2011 | Gueckel | |
| 8,378,129 B2 | 2/2013 | Bhise et al. | |
| 8,546,297 B2 | 10/2013 | Rokicki et al. | |
| 9,227,174 B2 | 1/2016 | Heinl et al. | |
| 2009/0177000 A1 | 7/2009 | Natal et al. | |
| 2009/0270640 A1 | 10/2009 | Maurer et al. | |
| 2012/0264954 A1 | 10/2012 | Rosendahl et al. | |
| 2013/0296587 A1 | 11/2013 | Rosendahl et al. | |
| 2014/0088316 A1* | 3/2014 | Natal ....................... | B01J 37/16 |
| | | | 549/534 |
| 2014/0179516 A1 | 6/2014 | Nakashiro et al. | |
| 2014/0187417 A1 | 7/2014 | Pak | |
| 2015/0174554 A1* | 6/2015 | Cao ........................ | B01J 23/688 |
| | | | 502/348 |
| 2018/0021755 A1 | 1/2018 | Suchanek | |
| 2019/0022628 A1* | 1/2019 | Pak .......................... | B01J 37/08 |

FOREIGN PATENT DOCUMENTS

| | | | | | |
|---|---|---|---|---|---|
| DE | 2300512 A1 | 7/1973 | | | |
| DE | 2454972 A1 | 6/1975 | | | |
| DE | 2521906 A1 | 12/1975 | | | |
| DE | 3414717 A1 | 10/1985 | | | |
| EP | 0014457 A2 | 8/1980 | | | |
| EP | 0082609 A1 | 6/1983 | | | |
| EP | 0085237 A1 | 8/1983 | | | |
| EP | 0172565 A2 | 2/1986 | | | |
| EP | 0266015 A1 | 5/1988 | | | |
| EP | 0339748 A2 | 11/1989 | | | |
| EP | 0357293 A1 | 3/1990 | | | |
| EP | 0480538 A1 | 4/1992 | | | |
| EP | 0716884 A2 | 6/1996 | | | |
| EP | 0902726 A1 | 3/1999 | | | |
| EP | 1115486 A1 | 7/2001 | | | |
| EP | 0902726 B1 | 10/2001 | | | |
| EP | 1393801 A1 * | 3/2004 | ............ | B01J 23/686 | |
| EP | 1478458 A1 | 11/2004 | | | |
| EP | 1613428 A2 | 1/2006 | | | |
| EP | 1675678 A1 | 7/2006 | | | |
| EP | 1893331 A1 | 3/2008 | | | |
| EP | 1511563 B1 | 11/2012 | | | |
| EP | 3254576 A1 | 12/2017 | | | |
| JP | 2005052838 A * | 3/2005 | ............. | B01J 21/04 | |
| WO | 97/46316 A1 | 12/1997 | | | |
| WO | WO-0015334 A1 | 3/2000 | | | |
| WO | 03/72244 A1 | 9/2003 | | | |
| WO | WO-03072244 A1 | 9/2003 | | | |
| WO | 2004/089537 A2 | 10/2004 | | | |
| WO | WO-2004089539 A1 | 10/2004 | | | |
| WO | 2004/094055 A2 | 11/2004 | | | |
| WO | 2004/101144 A1 | 11/2004 | | | |
| WO | 2005/039757 A1 | 5/2005 | | | |
| WO | WO-2006036667 A1 | 4/2006 | | | |
| WO | WO-2006133183 A2 | 12/2006 | | | |
| WO | 2007/000664 A1 | 1/2007 | | | |
| WO | 2007/021472 A2 | 2/2007 | | | |
| WO | WO-2007123932 A2 | 11/2007 | | | |
| WO | WO-2007122090 A3 | 2/2008 | | | |
| WO | 2008/054654 A2 | 5/2008 | | | |
| WO | 2009/029414 A1 | 3/2009 | | | |
| WO | 2009/029419 A1 | 3/2009 | | | |
| WO | 2010/008920 A2 | 1/2010 | | | |
| WO | WO-2010123729 A2 | 10/2010 | | | |
| WO | WO-2010123856 A1 | 10/2010 | | | |
| WO | 2011/153390 A2 | 12/2011 | | | |
| WO | WO-2012091898 A2 | 7/2012 | | | |
| WO | 2012/140614 A1 | 10/2012 | | | |
| WO | 2012/143557 A1 | 10/2012 | | | |
| WO | 2012/143559 A1 | 10/2012 | | | |
| WO | 2013/066557 A1 | 5/2013 | | | |
| WO | 2013/077839 A1 | 5/2013 | | | |
| WO | WO-2013061294 A1 | 5/2013 | | | |
| WO | 2014/105770 A1 | 7/2014 | | | |
| WO | 2015/095508 A1 | 6/2015 | | | |

OTHER PUBLICATIONS

International Preliminary Report on Patentability received for PCT Patent Application No. PCT/EP2019/052918, mailed on Feb. 10, 2020, 5 pages.

International Search Report and Written Opinion received for PCT Patent Application No. PCT/EP2019/052918, mailed on May 24, 2019, 9 pages.

International Search Report for PCT/EP2019/052866 mailed Apr. 25, 2019.

International Search Report for PCT/EP2019/052918 mailed May 24, 2019.

Written Opinion of the International Searching Authority for PCT/EP2019/052866 mailed Apr. 25, 2019.

Written Opinion of the International Searching Authority for PCT/EP2019/052918 mailed May 24, 2019.

U.S. Appl. No. 16/968,542, filed Aug. 7, 2020, Karpov et al.

* cited by examiner

METHOD FOR PREPARING A SILVER IMPREGNATION SOLUTION

CROSS-REFERENCE TO RELATED APPLICATIONS

This application is a national stage application (under 35 U.S.C. § 371) of PCT/EP2019/052918, filed Feb. 6, 2019, which claims benefit of European Application No. 18155566.5, filed Feb. 7, 2018, both of which are incorporated herein by reference in their entirety.

DESCRIPTION

The present invention relates to a method for preparing a silver impregnation solution and to a method for producing a catalyst effective in the oxidative conversion of ethylene to ethylene oxide.

It is known to prepare supported silver catalysts which are effective in the oxidative conversion of ethylene to ethylene oxide by treating a suitable support, in particular an alumina support, with a silver impregnation solution which optionally contains promotors. The impregnated support is then subjected to a calcination process.

Silver impregnation solutions of the art typically contain silver oxalate, or a combination of silver oxide and oxalic acid, together in ethylenediamine. In the oxalic acid formulation, oxalate in oxalic acid provides oxalate anion to counter the charge balance of silver cation in the ethylenediamine/water solution to form a soluble $[Ag_2C_2O_4]$—ethylenediamine complex.

One approach for preparing suitable silver impregnation solutions involves the preparation of insoluble silver oxalate intermediate starting from aqueous silver nitrate solutions. The silver oxalate intermediate is then dissolved in an aqueous solution of an organic amine which converts the silver oxalate into water soluble complexes. Ethylenediamine is a suitable organic amine ligand. Much effort has gone into the development of processes based on this or similar approaches, see, for example, EP 0 716 884 A2, EP 1 115 486 A1, EP 1 613 428 A1, U.S. Pat. No. 4,731,350, WO 2004/094055 A2, and WO 2009/029419 A1. Nevertheless, large scale industrial application of this approach is not very efficient because it requires elaborate solid/liquid phase separation steps.

Another approach for preparing suitable silver impregnation solutions involves preparing an aqueous oxalic acid-organic amine solution by reacting oxalic acid with an organic amine in the presence of water and conducting a silver complex formation reaction by adding particulate silver oxide to the aqueous oxalic acid-organic amine solution. This approach minimizes separation efforts. However, no suggestion has been made concerning a safe and efficient implementation of this approach into a technical process for the large-scale production of catalysts.

WO 2015/095508 A1, for example, describes the preparation of a silver solution in a laboratory scale. Water was gradually mixed with ethylenediamine in a container placed in an ice bath to control the solution temperature between 20 and 30° C. with vigorous agitation. Ammonium oxalate was subsequently added to the solution while the temperature was maintained at 20 to 30° C. After ammonium oxalate was completely dissolved, silver oxide was added to the solution at a temperature between 20 and 30° C. Comparative example 5 of WO 2015/095508 A1 provides a recipe for the preparation of a silver complex solution using oxalic acid as an exclusive source of oxalate ions. The amounts of oxalic acid dihydrate and silver oxide of 261.0 g and 490.0 g, respectively, correspond to an oxalic acid/silver molar ratio of 0.49.

U.S. Pat. No. 4,356,312 mentions that reagent grade silver oxide was mixed with an aqueous solution of reagent grade oxalic acid dissolved in ethylenediamine (EN) to form an about 2 molar solution of $Ag_2(EN)_2C_2O_4$. Ten percent by volume of ethanolamine (about 0.4 moles of ethanolamine per mole of silver) was then added to complete the solubilizing/reducing agent combination. This solution contained about 22% by weight silver.

US 2009/0177000 A1 describes that, for example, silver oxide can be dissolved in a solution of oxalic acid and ethylenediamine up to silver content of approximately 30 percent by weight.

U.S. Pat. Nos. 5,187,140, 4,908,343 and 5,504,053 describe in a very general way that a desired amount of ethylenediamine is mixed with distilled water. Then oxalic acid dihydrate is added slowly to the solution at ambient temperature while continuously stirring. Silver oxide powder is then added to the diamine-oxalic acid salt-water solution while maintaining the solution temperature below about 40° C. Finally, monoethanolamine, aqueous alkali metal salt solution(s) and distilled water are added to complete the solution. Nothing is said about any problem that might occur when this preparation of impregnation solution is applied at large industrial scale.

WO 2014/105770 A1 describes the preparation of an impregnation stock solution. 277.5 g of deionized water was placed in cooling bath to maintain temperature during the whole preparation under 50° C. At continuous stirring, 221.9 g of ethylenediamine was added in small portions to avoid overheating. 174.1 g of oxalic acid dihydrate was then added to the water-ethylenediamine solution in small portions. After all oxalic acid was dissolved, 326.5 g of high purity silver oxide was added to solution in small portions. After all silver oxide was dissolved and the solution was cooled to about 35° C. it was removed from cooling bath. The oxalic acid/silver molar ratio was 0.49.

The above described processes involve the handling of powders of oxalic acid and silver oxide. Both powders tend to be hygroscopic and can adhere to the inner walls of the feeding equipment and/or the reactor inner walls above the liquid level in the reactor. The latter phenomenon is aggravated by intense stirring, when particulate oxalic acid and/or silver oxide are flung around in the reactor and small quantities thereof come into contact with and adhere to the reactor inner walls. If dry or moist remains of oxalic acid adhering to inner walls of the feeding equipment and/or the reactor inner walls come into contact with silver oxide both chemicals can react to yield silver oxalate. Silver oxalate, however, is explosive upon heating, shock or friction. Thus, the preparation of a silver impregnation solution by subsequently adding oxalic acid and silver oxide to an aqueous amine solution, using the same powder feeding equipment or the same reactor runs the risk of severe security hazards.

It is an object of the present invention to provide a method for preparing a silver impregnation solution in an efficient and occupationally and environmentally safe way.

This problem is solved by a method for preparing a silver impregnation solution comprising:

(a) charging a neutralization reactor R1 with an aqueous organic amine;

(b) adding oxalic acid powder through a first feeding conduit to the neutralization reactor R1 to obtain an aqueous oxalic acid-organic amine solution;

(c) directing the aqueous oxalic acid-organic amine solution from the neutralization reactor R1 to a complexation reactor R2;

(d) adding particulate silver oxide through a second feeding conduit to the complexation reactor R2 to obtain a silver impregnation solution; and, optionally, (e) subjecting the silver impregnation solution to filtration.

The process avoids the possibility of oxalic acid and silver oxide powder coming into direct contact.

In step (a), a neutralization reactor R1 is charged with an aqueous organic amine. Any reactor known to those skilled in the art can be used. Such reactors comprise refrigerating means for cooling the reaction medium in the reactor and agitating means for agitating or stirring the reaction medium in the reactor. Stirred tank reactors can, for example, be used as reactors. Alternatively, a tank-type forced circulation reactor with a heat exchanger arranged in the external liquid circuit can be used.

Generally, an aqueous stock solution of the amine can be used which can be adjusted to the desired amine concentration by adding additional amine or water. Alternatively, the organic amine is dissolved in water in order to form an aqueous solution of the organic amine. Preferably, the organic amine concentration is in the range from 40 to 70 wt. %, in particular 50 to 62 wt. %.

Any organic amine can be used in the method of the invention which is capable of dissolving silver cations ($Ag^+$) in the form of a water soluble complex. The organic amine comprises, for example, a vicinal alkylene diamine, preferably ethylenediamine. Vicinal alkylene diamine, and in particular ethylenediamine, are capable of dissolving large amounts of silver oxalate in aqueous solutions. It is assumed that the free electron pairs of both nitrogen atoms of vicinal alkylene diamines coordinate to a silver cation thereby forming five-membered chelate rings.

Additional amines, such as monethanolamine, can be used if desired.

In step (b), oxalic acid powder is added through a first feeding conduit to the neutralization reactor R1, preferably on a metered basis. Oxalic acid can be added in any form. It is preferably added in the form of oxalic acid dihydrate. Known devices for dispensing powder materials, preferably on a metered basis, can be used such as loss-in-weight feeder systems or volumetric feeders.

Although the method of the invention can be carried out with oxalic acid dihydrate particles having a broad range of different sizes, ranging, for example, from the nanometer to the upper micrometer range, the oxalic acid dihydrate powder preferably has a controlled particle size distribution in order to operate the reaction of oxalic acid dihydrate with an aqueous organic amine solution in a controllable way. It is generally preferred that the oxalic acid dihydrate powder has a primary particle size distribution such that at least 75% by volume of the particles have a particle size of 250 μm or lower. Preferably, at least 75% by volume of the particles have a particle size of 50 μm or lower. "Primary particle size distribution" as used herein is measured using a dispersion pressure of equal or greater than 3.5 bar. Dispersion at a dispersion pressure of 3.5 bar resulted in a monomodal distribution which is used as the primary particle size distribution.

The oxalic acid dihydrate powder may, for example, have an agglomerated particle size distribution such that at least 75% of the total volume of oxalic acid dihydrate is in the form of aggregates having an apparent particle size of at least 50 μm. "Agglomerated particle size distribution" as used herein is measured using a dispersion pressure of 0.1 bar. When the oxalic acid dihydrate powder comprises a majority of small unagglomerated primary oxalic acid dihydrate powder particles, a dust of oxalic acid dihydrate can be formed during handling. Such dust formation is undesired as the dust particles can create health hazards or deposit on surfaces of the reaction equipment. It has been found that primary oxalic acid dihydrate powder particles having sizes of from the upper nanometer to lower micrometer range form aggregates having an apparent particle size in the upper micrometer to lower millimeter range and which are stable when exposed to a dispersion pressure of 0.1 bar in laser diffraction particle size analysis. Under feeding conditions the aggregates are stable and undesired dust formation can be suppressed.

The presence of metal species or of inorganic anions in the impregnation solution can adversely influence the catalytic properties of a catalyst produced therefrom. Although individual catalytic properties may be enhanced by a specific promoting species if purposively added to the impregnation solution other catalytic properties may be diminished. For that reason it is preferred to minimize the introduction of metal species or of inorganic anions via the oxalic acid dihydrate powder. Preferably, the oxalic acid dihydrate has a purity of at least 99.5% by weight.

The oxalic acid dihydrate contains, for example, 10 ppmw or less of copper.

The oxalic acid dihydrate contains, for example, 10 ppmw or less of iron.

The oxalic acid dihydrate contains, for example, 2 ppmw or less of lead.

The oxalic acid dihydrate contains, for example, 10 ppmw or less of sodium.

The oxalic acid dihydrate can contain varying amounts of sulfate ions. Sulphur is often added to the solution in minor controlled amounts, with the aim of improving catalyst selectivity. Excessive amounts of Sulphur, on the other hand, can cause catalyst poisoning. A preferred oxalic acid dihydrate contains 1500 ppmw or less, such as 500 ppmw or less, more preferable 100 ppmw or less, most preferably 20 ppmw or less of sulfate anions.

The reaction medium is generally agitated in step (b). Any agitation technique can be used which ensures sufficient mixing of the oxalic acid with the surrounding liquid. Agitation preferably involves stirring. As the reaction amines with oxalic acid is exothermic, it is important to cool the reaction in order to ensure that the oxalic acid-organic amine solution is prepared in a controlled way.

In an embodiment, prior to step (b), the aqueous organic amine is adjusted to a temperature $T_1$, wherein $T_1 \leq 100°$ C.$-\Delta T_{AD-1}$ and $\Delta T_{AD-1}$ is the maximum adiabatic temperature rise during step (b). The maximum adiabatic temperature rise $\Delta T_{AD-1}$ is the increase of the temperature of the reaction medium which would occur if the total amount of oxalic acid were added at once under adiabatic conditions.

The volatility of the organic amine is high at temperatures above 100° C. Excess vaporization of the organic amine can cause an uncontrolled pressure increase or the formation of explosive amine vapor/air mixtures. At a temperature of 100° C. or below, the reaction mixture can be safely handled over a period of at least 24 hours. If the method is carried out within the limitations of the above condition, the temperature of the reaction medium can never exceed 100° C. even if heat removal from the reaction medium is insufficient and/or heat removal equipment fails. This ensures a safe and efficient production of the aqueous oxalic acid-organic amine solution.

$\Delta T_{AD\text{-}1}$ can be calculated according to $$\Delta T_{AD\text{-}1} = Q_{AD\text{-}1}/m_1 * cp_1,$$

wherein $Q_{AD\text{-}1}$ is the reaction enthalpy of the organic amine-oxalic acid reaction, mi is the total weight and cpi the specific heat capacity, respectively, of the aqueous oxalic acid-organic amine solution, i.e. the reaction mixture in the neutralization reactor R1 after addition of the entire amount of oxalic acid. Conveniently, $Q_{AD\text{-}1}$ and $cp_1$ are determined experimentally, as illustrated in the appended examples. Typically, the reactants are present in non-stoichiometric amounts, and $Q_{AD\text{-}1}$ is determined by the reaction limiting reactant, typically the oxalic acid.

Preferably, the starting temperature $T_1$ is in the range from 10° C. to 40° C., particularly 10 to 20° C.

In step (c), the aqueous oxalic acid-organic amine solution is at least partially withdrawn from the neutralization reactor and directed to a complexation reactor R2 that is spatially separated from the vessel R1. This prevents any possibility of a direct reaction of oxalic acid powder with silver oxide powder. Any reactor known to those skilled in the art can be used as vessel R2. Such reactors comprise refrigerating means for cooling the reaction medium in the reactor and agitating means for agitating or stirring the reaction medium in the reactor. A stirred tank reactor can, for example, be used as reactor R2. Withdrawal of the aqueous oxalic acid-organic amine solution can occur by gravity, but is preferably effected by a liquid pump.

In the practice of the invention, it is not necessary to completely empty the neutralization reactor R1. Only a part of the aqueous oxalic acid-organic amine solution can be withdrawn and directed to the complexation reactor R2. The remainder of the solution in the neutralization reactor R1 can be supplemented with fresh amine and oxalic acid can be added in accordance with step (b).

In addition, spatial separation of step (b) from step (d) allows for efficient use of the capacity of each reactor. According to the invention, it is envisaged to provide one complexation reactor R2 or more than one complexation reactors $R2_1, \ldots R2_i$, for example a first complexation reactor R21 and a second complexation reactor R22, per one neutralization reactor R1. If more than one complexation reactors R2 are employed, these vessels are charged with the aqueous oxalic acid-organic amine solution at the same time or alternately, preferably alternately. Each of the complexation reactors $R2_i$ is equipped with a second feeding conduit for metering particulate silver oxide to the complexation reactor $R2_i$. Step (b) is inherently faster than step (d). The aqueous oxalic acid-organic amine solution is kept in the neutralization reactor R1 until the silver complex formation is substantially completed and the entire silver impregnation solution is withdrawn from the complexation reactor R2. If two complexation reactors R21 and R22 are available, while the reaction according to step (d) is ongoing in the first complexation reactor R21, aqueous oxalic acid-organic amine solution is withdrawn from the neutralization reactor into the second complexation reactor R22. Thus, delays in the operation of the neutralization reactor R1 caused by keeping the aqueous oxalic acid-organic amine solution in the neutralization reactor are shortened. The neutralization reactor R1 is available for refilling more frequently.

The reaction in step (d) proceeds to substantial completion relatively quickly and the complexation reactor R2 can be refilled frequently and, hence, can be operated with a high space-time yield. It has been found that a similar improvement of space-time-yield is achieved for the neutralization reactor R1 and the delays in use of the neutralization reactor R1 caused by keeping the aqueous oxalic acid-organic amine solution in the first reactor are shortened.

Further, spatial separation of steps (b) and (d) can increase the safety even further because the reactors can be adapted independently to the specific requirements of the chemical reactions which occur in step (b) and in step (d). This results in optimized control of the chemical reactions of step (b) in the neutralization reactor R1 and of the chemical reactions of step (d) in the complexation reactor R2.

In step (d), particulate silver oxide is added through a second feeding conduit to the complexation reactor R2, preferably on a metered basis, to obtain a silver impregnation solution. The particular silver oxide can be added to the aqueous oxalic acid-organic amine solution in portions or continuously. Known devices for dispensing powder materials, preferably on a metered basis, can be used such as loss-in-weight feeder systems or volumetric feeders. A silver complex formation reaction is conducted by adding particulate silver oxide to the aqueous oxalic acid-organic amine solution. This reaction involves the dissolution of silver oxide particles and complexation of silver cations.

The reaction medium is generally agitated in step (d). Any agitation technique can be used which ensures sufficient mixing of particulate silver oxide with the surrounding liquid. Agitation preferably involves stirring.

As the reaction of an aqueous oxalic acid-amine solution with silver oxide is exothermic, it is important to cool the reaction mixture during and immediately after the addition of the silver oxide in order to ensure that the aqueous silver complex suspension or solution is prepared in a controlled way. On the other hand, once the entire amount of silver oxide has been added to the complexation reactor R2 and the reaction temperature profile has passed the peak temperature, cooling is no longer required and can be discontinued. Preferably, cooling is switched to heating to control the reaction temperature to facilitate completion of the silver complexation reaction.

In an embodiment, prior to step (d), the aqueous oxalic acid-organic amine solution is adjusted to a temperature $T_2$, wherein $T_2 \le 80°$ C.$-\Delta T_{AD\text{-}2}$ and $\Delta T_{AD\text{-}2}$ is the maximum adiabatic temperature rise during step (d).

The inventors have found that an irreversible decomposition of the silver complexes formed in step (d) occurs at elevated temperatures and this irreversible decomposition is accelerated at temperatures above 80° C. Additionally, occupational or environmental hazards are more likely to occur at temperatures above 80° C.

The maximum adiabatic temperature rise $\Delta T_{AD\text{-}2}$ is the increase of the temperature of the reaction medium which would occur if the total amount of silver oxide were added at once and converted in the silver complex formation reaction under adiabatic conditions.

$\Delta T_{AD\text{-}2}$ can be calculated according to $$\Delta T_{AD\text{-}2} = Q_{AD\text{-}2}/m_2 * cp_2,$$

wherein $Q_{AD\text{-}1}$ is the reaction enthalpy of the silver complex formation reaction, $m_2$ is the total weight and $cp_2$ is the specific heat capacity, respectively, of the silver impregnation solution, i.e. the reaction mixture in the complexation reactor R2 after addition of the entire amount of silver oxide. Conveniently, $Q_{AD\text{-}2}$ and $cp_2$ are determined experimentally, as illustrated in the examples. Typically, the reactants are present in non-stoichiometric amounts, and $Q_{AD\text{-}2}$ is determined by the reaction limiting reactant, typically the silver oxide.

If step (d) is carried out within the limitations of the above condition, undesired irreversible decomposition of silver complexes is suppressed because the temperature of the reaction medium can never exceed 80° C. even if heat removal from the reaction medium is insufficient and/or heat removal equipment fails. This ensures a safe and efficient production of the silver impregnation solution.

In a process, wherein oxalic acid powder and particulate silver oxide are subsequently metered into only one reactor, a maximum adiabatic temperature rise in the magnitude of $\Delta T_{AD\text{-}1} + \Delta T_{AD\text{-}2}$ could occur, in case the metering equipment and/or heat removal equipment fails. Such temperature rise is difficult to manage and can give rise to severe occupational or environmental hazards.

Preferably, the starting temperature $T_2$ is in the range from 10° C. to 40° C., particularly 15 to 20° C.

According to the invention, the silver complex formation rates are high. Preferably, the time period of step (d) does not exceed 3 minutes per kg of added silver oxide, calculated as Ag metal. In particular, the time period does not exceed 2 minutes per kg of added silver oxide, in particular not exceed 90 seconds per kg of added silver oxide, calculated as Ag metal.

In preferred methods of the invention, the method involves the addition of at least 100 kg of particulate silver oxide, preferably at least 200 kg of particulate silver oxide, in particular at least 300 kg, calculated as Ag metal.

The silver oxide particles or powder can, for example, be essentially dry, or be a damp (moist) powder. The moist powder can contain substantial amounts of water. High moisture contents are tolerated by the method of the invention. The silver oxide may, for example, have a water content of up to 20% by weight, preferably, up to 15% by weight. The "water content" as used herein includes water which is physically adsorbed to the silver oxide and water which is chemically bound, for example, in the form of hydroxide. A skilled person can measure the water content of particulate silver oxide according to methods well-known in the art and calculate very easily how much water is added into the reaction medium as a part of moist silver oxide.

Although the method of the invention can be carried out with silver oxide particles having a broad range of different sizes, ranging, for example, from the nanometer to the upper micrometer range, the silver oxide preferably has a controlled particle size distribution in order to facilitate the dissolution of the silver oxide and complexation of the silver cations. It is generally preferred that the silver oxide has a primary particle size distribution such that at least 75% by volume of the particles have a particle size of 250 µm or lower. Preferably, at least 75% by volume of the particles have a particle size of 50 µm or lower. Most preferably, at least 75% by volume of the particles have a particle size of 10 µm or lower. "Primary particle size distribution" as used herein is measured using a dispersion pressure of 3.5 bar. Dispersion at a dispersion pressure of 3.5 bar resulted in a monomodal distribution which is used as the primary particle size distribution.

The particulate silver oxide powder may, for example, have an agglomerated particle size distribution such that at least 30% by volume, preferably at least 75% by volume of silver oxide is in the form of aggregates having an apparent particle size of at least 50 µm, e.g. at least 100 µm. "Agglomerated particle size distribution" as used herein is measured using a dispersion pressure of 0.1 bar. When the particulate silver oxide comprises a majority of small unagglomerated primary silver oxide particles, a dust of silver oxide particles can be formed during handling. Such dust formation is undesired as the dust particles can create health hazards or deposit on surfaces of the reaction equipment. It has been found that primary silver oxide particles having sizes of from the upper nanometer to lower micrometer range form aggregates having an apparent particle size in the upper micrometer to lower millimeter range and which are stable when exposed to a dispersion pressure of 0.1 bar in laser diffraction particle size analysis. Under feeding conditions the aggregates are stable and undesired dust formation can be suppressed.

Preferably, the silver oxide has a controlled BET specific surface area range. The specific surface area is the total surface area of the silver oxide particles expressed in square meters per mass of silver oxide particles expressed in gram. The particulate silver oxide can, for example, have a specific surface area in the range of 0.1 m²/g to 10 m²/g, e.g., at least 0.2 m²/g to 5 m²/g, preferably, at least 0.3 m²/g to 1.0 m²/g.

It is assumed that the surface area of silver oxide which is in contact with the liquid reaction medium influences the silver complex formation kinetics. An increased silver oxide surface area results in an accelerated silver complex formation reaction. On the other hand, too high surface area results in dust formation and can create health hazards.

The presence of metal species other than silver and/or of inorganic anions in the impregnation solution can adversely influence the catalytic properties of a catalyst produced therefrom. Although individual catalytic properties may be enhanced by a specific promoting species if purposively added to the impregnation solution other catalytic properties may be diminished. For that reason it is preferred to minimize the introduction of metal species other than silver and/or of inorganic anions via the silver oxide.

Preferably, the silver oxide has a purity of at least 99.5% by weight, in particular at least 99.9% by weight.

A preferred silver oxide contains 500 ppmw or less of the sum of chloride and sulfate anions.

The silver oxide contains, for example, 15 ppmw or less of chloride anions.

The silver oxide contains, for example, 20 ppmw or less of sulfate anions.

The silver oxide contains, for example, 100 ppmw or less of nitrates.

A preferred silver oxide contains 500 ppmw or less of trace metals selected from copper, iron, lead, nickel, and sodium.

The silver oxide contains, for example, 10 ppmw or less of copper.

The silver oxide contains, for example, 10 ppmw or less of iron.

The silver oxide contains, for example, 10 ppmw or less of lead.

The silver oxide contains, for example, 10 ppmw or less of nickel.

The silver oxide contains, for example, 10 ppmw or less of sodium.

A particularly preferred silver oxide contains 15 ppmw or less of chlorides, 100 ppmw or less of nitrates, 20 ppmw or less of sulfates, 5 ppmw or less of copper, 5 ppmw or less of iron, 5 ppmw or less of lead, 5 ppmw or less of nickel and 5 ppmw or less of sodium.

The relative amounts of water, organic amine, oxalic acid and silver oxide are not especially limited. Increasing the content of organic amine in excess over the stoichiometric amount does in general increase the solubility of silver cations in aqueous solutions containing oxalic acid.

An oxalate anion can counterbalance the charge of two silver cations and the amount of silver oxide and oxalic acid used in the method of the invention are preferably such that the oxalic acid/silver molar ratio is preferably in the range from 0.4 to 0.65, more preferably 0.5 to 0.6, in particular 0.505 to 0.6. It has been found that the amount of undissolved solids is minimized when the oxalic acid is used in a slight stoichiometric excess over the silver ions. Using an excess of oxalic acid allows for a reduction of the residence time required for step (d). Thus, production of a silver impregnation solution having a given amount of undissolved $Ag_2O$ proceeds faster with an oxalic acid/silver molar ratio above 0.5, as compared to an oxalic acid/silver molar ratio of 0.5 or below.

In a preferred method of the invention, the molar ratio of amine nitrogen atoms of the organic amine to silver cations is at least 2.66, e.g., at least 2.76, preferably at least 2.86, most preferably at least 3.00. When the organic amine is a diamine, such as ethylenediamine, the molar ratio of diamine to silver cations is thus at least 1.33, e.g., at least 1.38, preferably at least 1.43, most preferably at least 1.50. It is assumed that a molar access of volatile organic amine is advantageous, because an increased concentration of organic amine accelerates the dissolution of silver oxide in step (c).

In the method of the invention, the amount of organic amine comprised by the silver complex formation reaction medium may, for example, be at least 23%, in particular at least 24% by weight, preferably at least 25% by weight, most preferably at least 26% by weight after addition of all the silver oxide. This amount is based on all organic amine in the reaction medium, e.g., coordinated and uncoordinated.

Although the method of the invention is not limited to silver impregnation solutions having a particular content of dissolved, e.g., complexed silver cations, it is generally preferred to prepare silver impregnation solutions having a high dissolved silver content. In a preferred method of the invention, the finished silver impregnation solution contains 24 to 35% by weight, e.g. 25 to 34% by weight, in particular 26 to 33% by weight, preferably 27 to 32% by weight, more preferably 28 to 31% by weight and most preferably 29 to 30% by weight of dissolved, e.g., complexed, silver cations. The content of dissolved silver cations is calculated based on all silver cations which are homogeneously dissolved in the reaction medium at the end of the silver complex formation reaction.

The homogeneously dissolved silver cations comprise silver cations complexed by organic amine and silver cations dissolved in any other form.

After complete addition of silver oxide, agitation, preferably by stirring, is typically continued during a post-reaction period to drive the silver complex formation reaction to completion. Cooling is discontinued during the post-reaction. The post-reaction can be carried out under gentle heating, e.g. at a temperature in the range of 20 to 45° C., preferably 25 to 40° C. In order to minimize the risk of operation errors and to avoid a situation where the content of the complexation reactor R2 is heated while the addition of particulate sliver oxide is still ongoing, the post-reaction is preferably conducted in a post reactor R3 where the post reactor R3 is the only vessel equipped with heating means. Thus, in one embodiment the reaction medium obtained at the end of step (d) is transferred to a post reactor R3 and stirred for a post-reaction period, optionally under heating to a temperature of up to 45° C., for example 20 to 40° C.

In the practice of the invention, it is not necessary to completely empty the complexation reactor R2. Only a part of the suspension obtained at the end of step (d) can be withdrawn and directed to the post reactor R3 or filtration unit. The remainder of the solution in the complexation reactor R2 can be supplemented with fresh aqueous oxalic acid-organic amine solution and particulate silver oxide can be added in accordance with step (d).

The solution or suspension obtained at the end of step (d) can be used as a silver impregnation solution. If an insoluble solid is present in the reaction medium obtained at the end of step (d), the reaction medium can be subjected to filtration operation in a filtration unit (step (e)), preferably a clarification filtration operation. The silver impregnation solution can, for example, be obtained by passing the reaction medium through a filtration unit in order to remove a minor amount of undissolved solid which is present in reaction medium. Any known filtration technique can be used.

A depth filtration means is preferably used in the filtration operation. Depth filters are a variety of filters that use a porous filtration medium to retain particles throughout the medium. The depth filtration means can include one or more filters, such as membrane filters, plate filters, cartridge filters, bag filters, pressure leaf filters, rotary drum filters or vacuum filters. Different size particles can be trapped at different locations throughout the thickness of the filtration media. Larger particles are trapped on an outer layer with the subsequent layers trapping smaller and smaller particles until reaching the final desired micron rating. This prevents particle build-up from becoming so fine that plugging occurs and increases the particles-holding capacity of the filter, which gives the filter a longer life. Stacked disc modules are generally preferred due to their convenience of handling. As one example, SUPRAdisc® II Depth Filter Modules available from Pall Corporation, Port Washington, USA, such as Supradisc II KS 100, can effectively be used to remove undissolved solid from the silver impregnation solution.

According to the invention, it is envisaged to provide one filtration unit or more than one filtration units, for example two filtration units. Filtration of the the silver impregnation solution can be switched to and continued in a second filtration unit in case the first filtration unit is down for maintenance due to clogging or the like.

The method of the invention may comprise adding one or more promoting species to the impregnation solution. A promoting species denotes a component that provides an improvement in one or more of the catalytic properties of the catalyst prepared form the impregnation solution when compared to a catalyst not containing said component. The promoting species can be any of those species, known in the art, that function to improve the catalytic properties of the silver catalyst. Examples of catalytic properties include, inter alia, operability (resistance to runaway), selectivity, activity, conversion, stability and yield.

The promoting species may be added to the impregnating solution in any soluble form.

Sources for promoting species can be added into the reaction medium at any time from the beginning of step (a) to the end of step (e) or to any of the organic amine, the oxalic acid and/or the water before these are reacted in step (a) or after completion of step (e).

In some embodiments, the impregnation solution may include a promoting amount of an alkali metal or a mixture of two or more alkali metals. Suitable alkali metal promoters include, for example, lithium, sodium, potassium, rubidium, cesium or combinations thereof. Potassium is often preferred. The amount of alkali metal, e.g. potassium, will typically range from 50 ppm to 5000 ppm, more typically from 75 ppm to 3000 ppm, most typically from 100 ppm to 1000 ppm expressed in terms of the alkali metal relative to the weight of silver.

The impregnation solution may also include a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters can be used in amounts similar to those used for the alkali or transition metal promoters.

The impregnation solution may also include a promoting amount of a main group element or a mixture of two or more main group elements. Suitable main group elements include any of the elements in Groups IIIA (boron group) to VIIA (halogen group) of the Periodic Table of the Elements. For example, the carrier or catalyst can include a promoting amount of sulfur, phosphorus, boron, halogen (e.g., fluorine), gallium, or a combination thereof.

The impregnation solution may also include a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof. In one embodiment, the transition metal promoter(s) is (are) present in a total amount from 150 ppm to 15000 ppm, typically 225 ppm to 9000 ppm, most typically from 300 ppm to 3000 ppm, expressed in terms of metal(s) relative to the weight of silver.

Of the transition metal promoters listed, rhenium (Re) is a particularly efficacious promoter for ethylene epoxidation high selectivity catalysts. The rhenium component in the carrier or catalyst can be in any suitable form, but is more typically one or more rhenium-containing compounds (e.g., a rhenium oxide) or complexes.

The impregnation solution may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

A preferred promoting species is potassium which is preferably added in the form of a potassium salt, e.g., potassium hydroxide which can for example be fed into step (a) by adding it to an aqueous solution of organic amine, e.g. ethylenediamine, which is fed into step (a). Alternatively, a part of the potassium source is added in step (a) and another part is added to the silver impregnation solution after completion of step (d) or (e). If other promotors such as rhenium, tungsten, lithium, cesium and sulfur, are used, sources of these promotors are preferably added to the silver impregnation solution after completion of step (d) or (e).

Alternatively, the method of the invention does not comprise adding a promoting species.

The method of the invention may also comprise adding silver concentration enhancers such as ammonium salts having thermally decomposable anionic components as described in WO 2015/095508 A1.

The present invention further relates to a method for producing a catalyst effective in the oxidative conversion of ethylene to ethylene oxide, the method comprising (i) preparing a silver impregnation solution according to a method of the invention;

(ii) impregnating a refractory support with the silver impregnation solution; and (iii) subjecting the impregnated refractory support to a calcination process.

Any refractory support known in the art can be used. Suitable examples of refractory supports are described in EP 0902726, EP 1478458, EP 1675678, EP 3254576, WO 2004/101144, WO 2007/021472, WO 2008/054654, WO 2009/029414, WO 2010/008920, WO 2011/153390A1, WO 2012/143557A1, WO 2012/143559A1, WO 2013/077839A1 or US 2018/0021755.

Any impregnation processes known in the art can be used. A suitable example of an impregnation process is described in WO 2013/066557.

Any calcination processes known in the art can be used. Suitable examples of calcination processes are described in U.S. Pat. Nos. 5,504,052, 5,646,087, 7,553,795, 8,378,129, 8,546,297, US 2014/0187417, EP 1893331 or WO 2012/140614.

Impregnation step (ii) may comprise multiple alternating impregnation and drying steps. The impregnation solution in a first impregnation step comprises for example silver and promotor, e.g. potassium. Additional promotors, such as tungsten, rhenium, lithium, sulfur, and/or cesium can, for example, be comprised by a silver impregnation solution used in a second or later impregnation step.

The invention will be described in more detail by the accompanying drawings and the subsequent examples.

A BRIEF DESCRIPTION OF THE FIGURES

Figure 1:
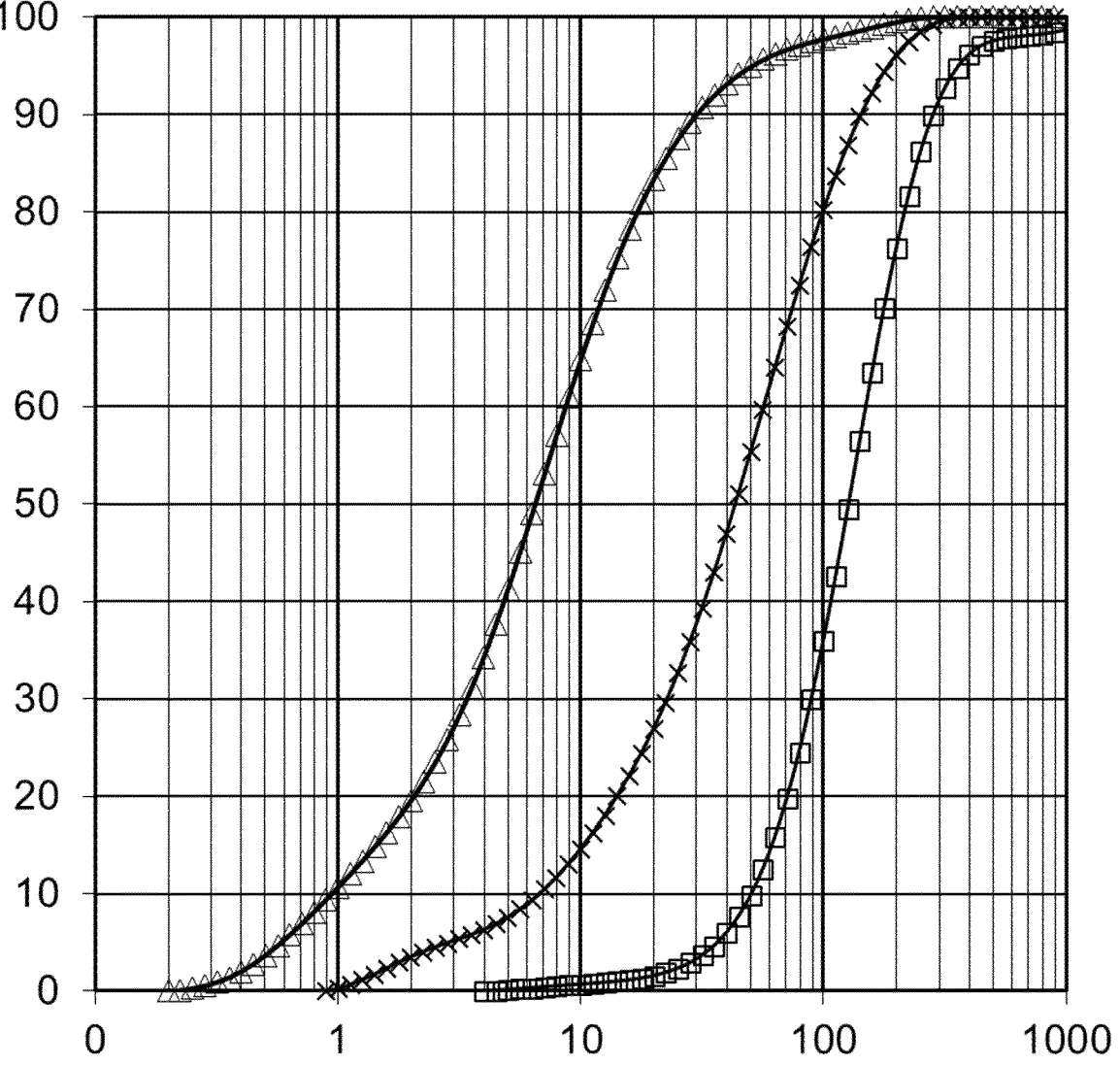
FIG. 1 shows a favorable particle size distribution of oxalic acid dihydrate powder using different dispersion pressures (squares=0.1 bar; crosses=1 bar; triangles=3.5 bar).
Figure 2:
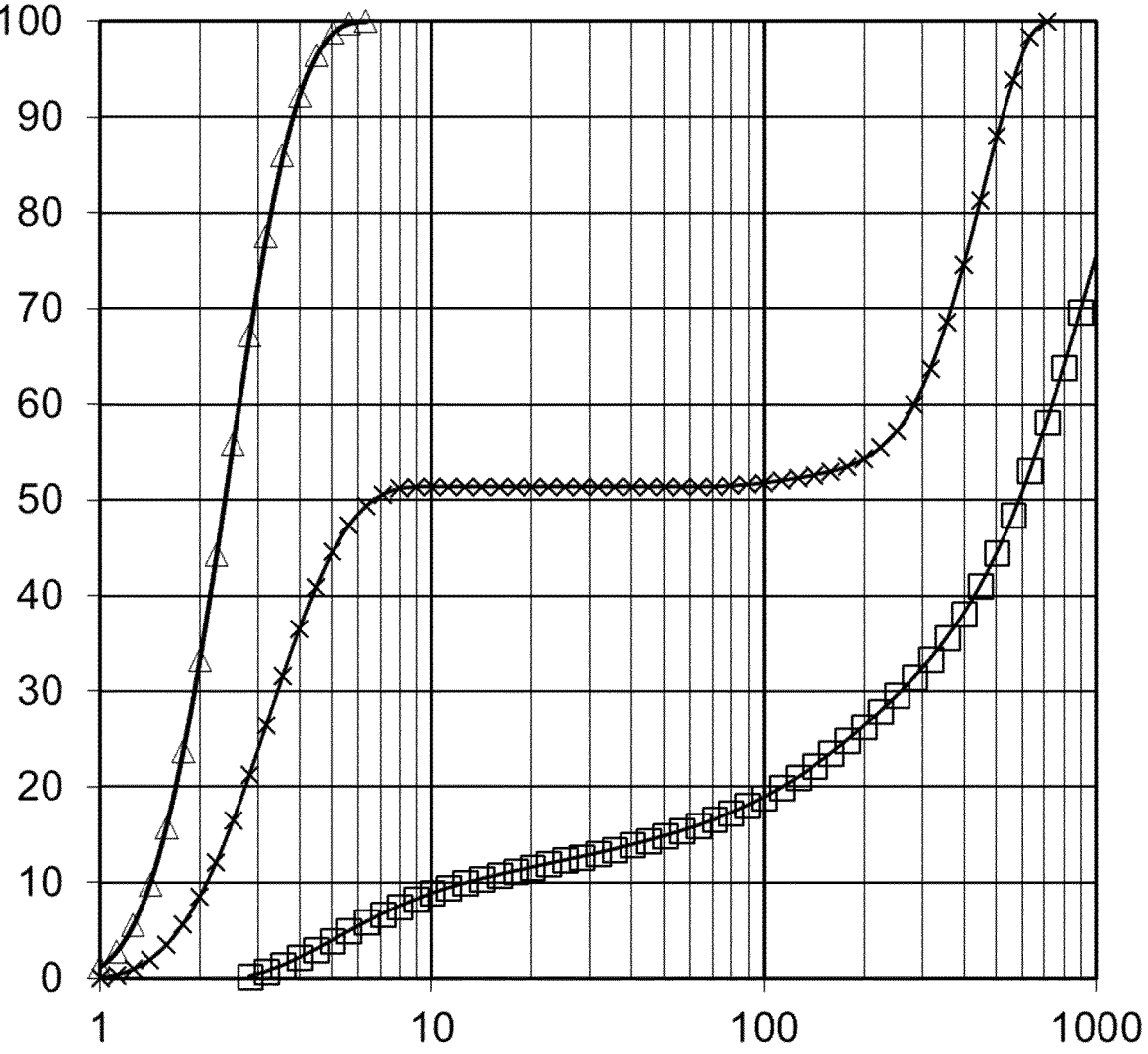
FIG. 2 shows a favorable particle size distribution of silver oxide powder using different dispersion pressures (squares=0.1 bar; crosses=1 bar; triangles=3.5 bar).

In FIGS. 1 and 2, the abscissa shows the particle size in μm on a logarithmic scale, and the ordinate shows the particular corresponding cumulative proportion of the particles in % by volume (the ordinate value of one point on the distribution curve shows the X% of the total particle volume which consists of particles having the particle size assigned to this point on the abscissa or having a smaller particle dimension; in other words, (100-X)% of the total particle volume consist of particles having a greater particle size.

Figure 3:
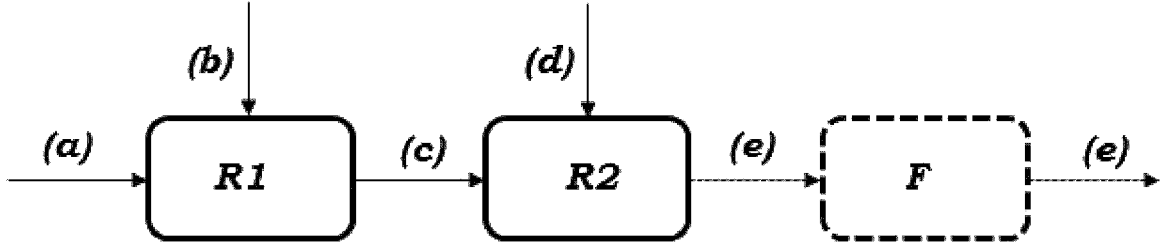
FIG. 3 shows a flow chart of an embodiment of the process of the invention.

According to FIG. 3, a neutralization reactor R1 is charged with an aqueous organic amine through line (a); then oxalic acid powder is metered through a first feeding conduit (b) to the neutralization reactor R1 to obtain an aqueous oxalic acid-organic amine solution; the aqueous oxalic acid-organic amine solution is withdrawn from the neutralization reactor R1 into a complexation reactor R2 through line (c); particulate silver oxide is metered through a second feeding conduit (d) to the complexation reactor R2 to obtain a silver impregnation solution; and the silver impregnation solution is withdrawn through line (e) and subjected to filtration in filtration unit F.

Figure 4:
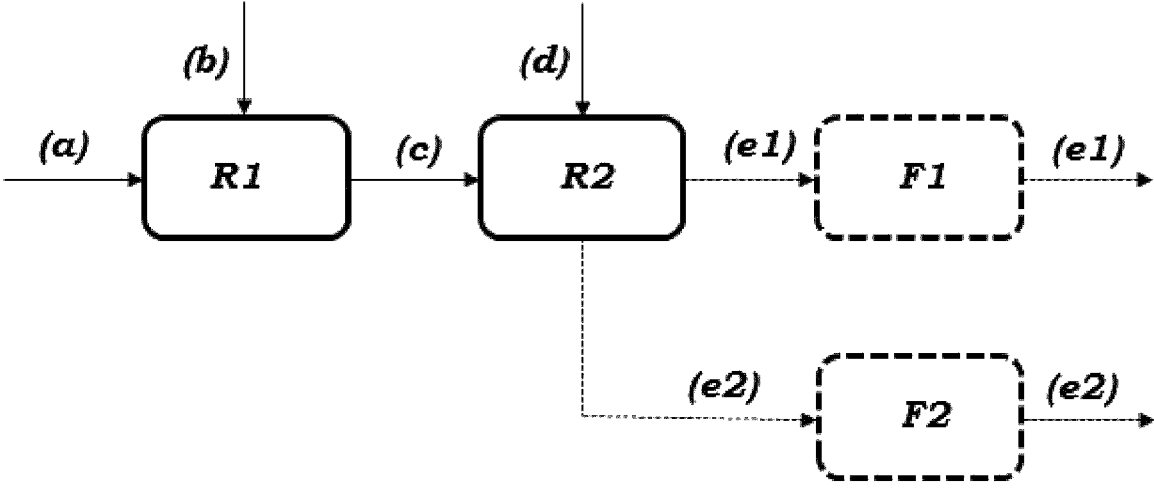
FIG. 4 shows a flow chart of an embodiment of the process of the invention including two filtration units F1 and F2.

According to FIG. 4, two filtration units F1 and F2 are provided. Filtration of the the the silver impregnation solution can be continued in filtration unit F2 in case filtration unit F1 is down for maintenance.

Figure 5:
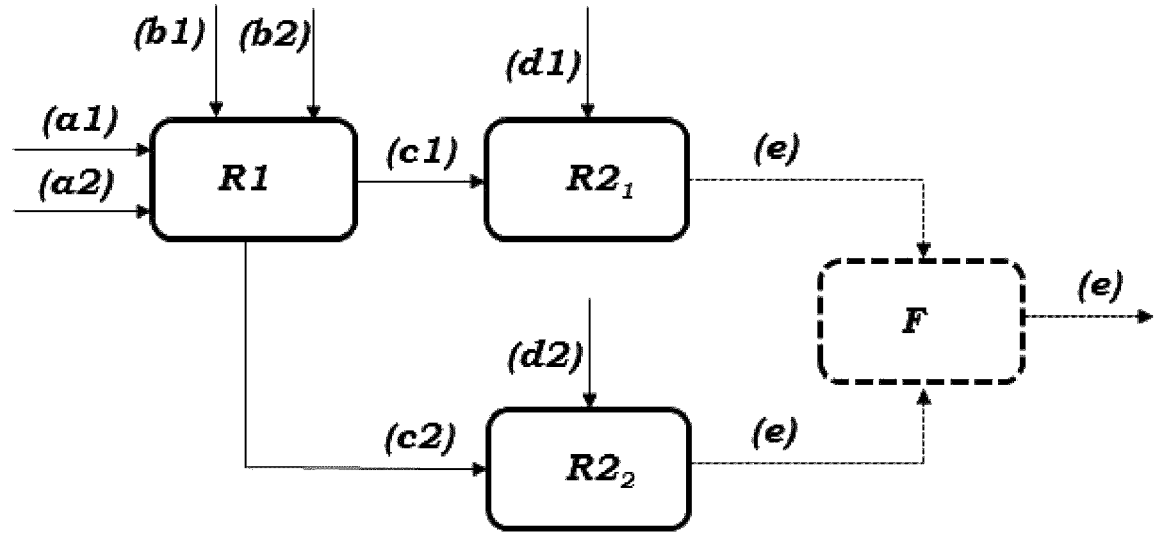
FIG. 5 shows a flow chart of an embodiment of the process of the invention including a first complexation reactor $R2_1$ and a second complexation reactor $R2_2$ which are operated alternately, and a common filtration unit.

According to FIG. 5, a first complexation reactor $R2_1$ and a second complexation reactor $R2_2$ are provided, which are operated alternately. Aqueous oxalic acid-organic amine solution is withdrawn from the neutralization reactor R1 into the first complexation reactor $R2_1$ and particulate silver oxide is metered through feeding conduit $(d_1)$ to the first complexation reactor $R2_1$. While metering of particulate silver oxide into the first complexation reactor $R2_1$ is ongoing, freshly prepared aqueous oxalic acid-organic amine solution is withdrawn from the neutralization reactor R1 into the second complexation reactor $R2_2$ and particulate silver oxide is metered through feeding conduit $(d_2)$ to the second complexation reactor $R2_2$. Silver impregnation solution is withdrawn through line (e) from complexation reactors $R2_1$ and $R2_2$ and subjected to filtration in filtration unit F.

Figure 6:
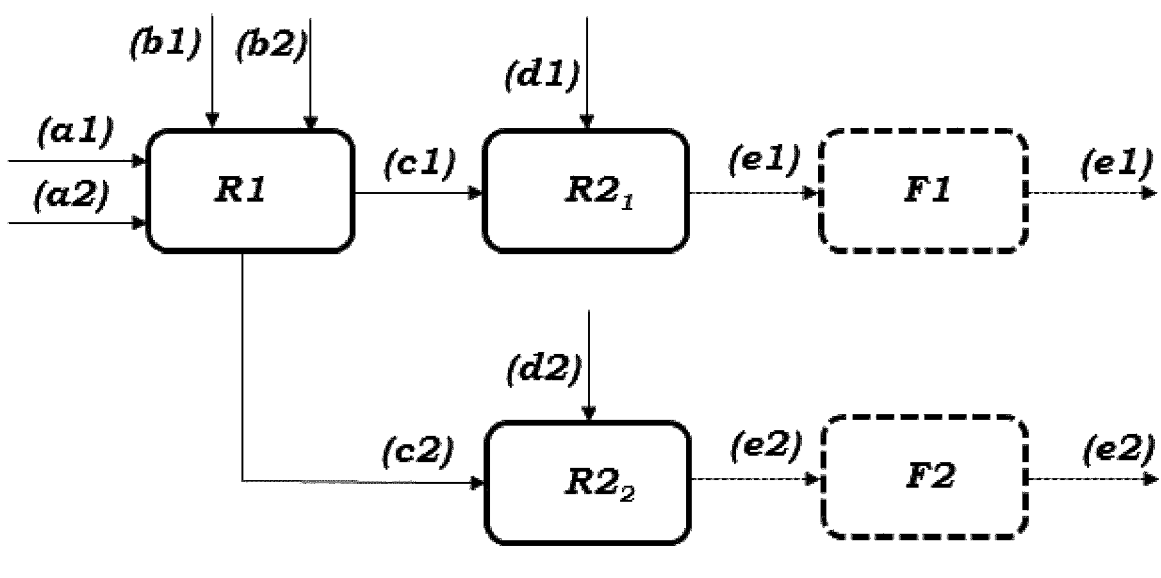
FIG. 6 shows a flow chart of an embodiment of the process of the invention including a first complexation reactor $R2_1$ and a second complexation reactor $R2_2$ which are operated alternately, and two filtration units F1 and F2.

FIG. 6 shows an embodiment of the invention similar to FIG. 5, however, two filtration units F1 and F2 are provided which are separately allocated to each of the complexation vessels $R2_1$ and $R2_2$.

Figure 7:
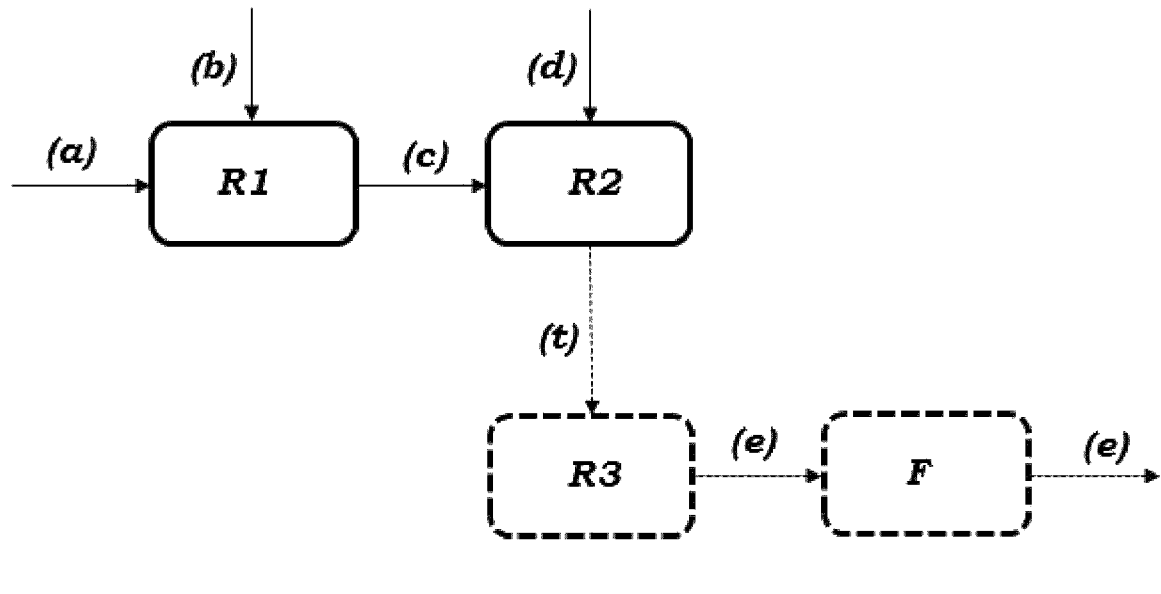
FIG. 7 shows a flow chart of an embodiment of the process of the invention including a third vessel R3.

FIG. 7 shows a flow chart of an embodiment of the process of the invention including a post reactor R3 for driving the silver complex formation reaction to completion.

Particle Size Distribution Measurements

The particle size distributions referred to herein are determined by laser diffraction. This involves passing the powder through a sieve in order to remove agglomerates of a size of more than 2 mm then conducting the sieved powder into a Scirocco 2000 dry powder feeder, dry-dispersing it therein with compressed air and blowing it into the test cell in a free jet. In this cell, a Malvern Mastersizer 2000 laser diffraction spectrometer is used to determine the volume-based particle size distribution to ISO 13320. The intensity of the dispersion of the dry powder during the analysis is determined by the dispersion pressure employed of the compressed air employed as the propellant gas. Dispersion pressures of 0.1 bar, 1 bar, and 3.5 bar (absolute pressure) have been used.

EXAMPLE 1

Silver Oxalate Reactivity

To assess the reactivity of $Ag_2O$ powder with oxalic acid dihydrate, the following experiments were devised:

Sample 1: 1.25 g oxalic acid dihydrate and 1.25 g $Ag_2O$ powder were mixed and allowed to react at room temperature for four hours.

Sample 2: 1.25 g oxalic acid dihydrate, 1.25 g $Ag_2O$ powder and 0.5 g deionized water were mixed and allowed to react at room temperature for four hours. The deionized water was preheated to 40° C. prior to mixing.

Both samples showed a visible reaction and were subjected to DSC analysis. The results are shown below:

| | Onset temperature [° C.] | Heat release [J/g] |
|---|---|---|
| Sample 1 | 125 | 300 |
| Sample 2 | 85 | 340 |

Thus, oxalic acid dihydrate and $Ag_2O$ powder can form thermally unstable silver oxalate that upon thermal decomposition releases a high amount of energy.

EXAMPLE 2

Determination of $Q_{AD-1}$, $cp_1$, $Q_{AD-2}$, and $cp_2$

Reaction enthalpies and heat capacities were measured in a microcalorimeter (RC1e manufactured by Mettler Toledo) as follows. 350.1 g (3.087 mol) 53 wt % ethylenediamine/$H_2O$ solution was charged into the reactor and tempered to 38° C. Then, 120.5 g (0.956 mol) oxalic acid dihydrate was added via a funnel in 5 identical portions of 24.1 g each within 20 sec and stirred for 6min at 38° C. The heat flow during the additions was recorded and $Q_{AD-1}$ was calculated. Then, $cp_1$ was determined.

Subsequently, 223.5 g (0.965 mol) silver(I)-oxid was added via a funnel in 5 identical portions of 44.7 g within 30 sec and stirred for 6min at 38° C. The heat flow during the additions was recorded and $Q_{AD-2}$ was calculated. Finally, $cp_2$ was determined.

The results are as follows:

$Q_{AD-1}$=−83.5 kJ/batch, $cp_1$=3,015 kJ/(kg*K), m=0.47 kg $\Delta T_{AD-1}$=$Q_{AD-1}$/(m*$cp_1$)=59 K $Q_{AD-2}$=−62 kJ/batch, $cp_2$=2,245 kJ/(kg*K), m=0.69 kg $\Delta T_{AD-2}$=$Q_{AD-2}$/(m*$cp_2$)=40 K

PRODUCTION EXAMPLE 1

783 kg of an aqueous ethylenediamine solution with an ethylenediamine content of 59 wt % was pumped in a stirring reactor 1. Subsequently the 59 wt % ethylenediamine solution was diluted under stirring with 94 kg of de-ionized water. Next, 26.6 kg of 0.95 wt % KOH solution were added to form an aqueous KOH/ethylenediamine solution. The solution was cooled to a temperature of below 20° C. Then 300 kg of oxalic acid dihydrate (purity 99.6%, particle size distribution is shown in FIG. 1) were added into the stirring reactor 1 stepwise during about 180 minutes under stirring and cooling to control the reaction temperature in the range of 20-25° C. Once the addition of oxalic acid dihydrate was completed and the temperature profile from the addition of the last portion of oxalic acid dihydrate passed a maximum, cooling was terminated and the reaction mixture was stirred further for the next 60 minutes to form an aqueous oxalic acid-ethylenediamine solution.

Next, 1113 kg of the resulting aqueous oxalic acid-ethylenediamine solution was transferred from the stirring reactor 1 to a stirring reactor 2. The reaction medium was cooled to a temperature below 20° C. Then, 500 kg silver oxide powder ($Ag_2O$-content 99.90 wt %, moisture content 0.2 wt %, particle size distribution is shown in FIG. 2, BET surface area=0.66 m²/g), was added during 225 minutes under stirring and cooling to control the reaction temperature in the range of 20-25° C. Once the addition of silver oxide was completed, and the temperature profile from the addition of the last portion of silver oxide passed a maximum, cooling was terminated and the reaction mixture was heated under stirring in a temperature range of about 25-30° C. for the next 3 hours to form an aqueous Ag complex suspension.

The silver oxide used is commercially available from Ames Goldsmith. Its chemical composition is described below:

| | |
|---|---|
| Silver Content as Ag$_2$O | ≥99.90% |
| moisture content | ≤0.20% |
| chlorides | ≤15 ppm |
| nitrates | ≤100 ppm |
| carbonates | ≤0.25% |
| sulfates | ≤20 ppm |
| copper | ≤20 ppm |
| iron | ≤20 ppm |
| lead | ≤20 ppm |
| nickel | ≤20 ppm |
| sodium | ≤50 ppm |
| other trace metals | ≤20 ppm |

Subsequently, the silver impregnation solution was obtained by passing the reaction mixture through a filtration unit SUPRAdisc® II KS 100 Depth Filter Modules available from Pall Corporation, Port Washington, USA to remove a minor amount of undissolved solid. The resulting silver impregnation solution had a density of 1.530 g/ml and a silver content of 29.5 wt %.

PRODUCTION EXAMPLE 2

844 kg of an aqueous ethylenediamine solution with an ethylenediamine content of 59.4 wt % was pumped in a stirring reactor 1. Subsequently the 59.4 wt % ethylenediamine solution was diluted under stirring with 113 kg of de-ionized water. Next, 28.8 kg of 0.95 wt % KOH solution were added to form an aqueous KOH/ethylenediamine solution. The solution was cooled to a temperature of below 20° C. Then 325 kg of oxalic acid dihydrate (purity 99.6%, particle size distribution is shown in FIG. 1) were added into the stirring reactor 1 stepwise during about 195 minutes under stirring and cooling to control the reaction temperature in the range of 20-25° C. Once the addition of oxalic acid dihydrate was completed, and the temperature profile from the addition of the last portion of oxalic acid dihydrate passed a maximum, cooling was terminated and the reaction mixture was stirred further for the next 60 minutes to form an aqueous oxalic acid-ethylenediamine solution.

Next, 1145 kg of the resulting aqueous oxalic acid-ethylenediamine solution was transferred from the stirring reactor 1 to a stirring reactor 2. The reaction medium was cooled to a temperature below 20° C. Then, 530 kg silver oxide powder (Ag$_2$O-content 99.90 wt %, moisture content 0.2 wt %, particle size distribution is shown in FIG. 2; purity as in Production example 1, BET surface area=0.66 m$^2$/g), was added during 240 minutes under stirring and cooling to control the reaction temperature in the range of 20-25° C. Once the addition of silver oxide was completed, and the temperature profile from the addition of the last portion of silver oxide passed a maximum, cooling was terminated and the reaction mixture was heated under stirring in a temperature range of about 25-30° C. for the next 6 hours to form an aqueous Ag complex suspension. The applied oxalate to silver molar ratio was 0.49. Despite of the increased heating time, the suspension contained a much higher amount of undissolved solid.

Subsequently, the reaction mixture was passed through a filtration unit SUPRAdisc® II KS 100 Depth Filter Modules available from Pall Corporation, Port Washington, USA to remove to the undissolved solid. However the filtration modules were plugged and it was difficult to obtain a silver complex solution.

Catalyst Preparation

Step 1. Preparation of Ag-Containing Intermediate 585 kg of a commercially available alpha-alumina support were placed in a vacuum tumble mixer having a volume of 1.8 m$^3$. The support had a cylindrical geometry with the cylinders having an outer diameter of 9 mm, a length of 9 mm and a wall thickness of 3 mm. The support had a water uptake of 0.55 ml/g and a BET surface area of 2 m$^2$/g. The support was impregnated with 468 kg of Ag complex solution prepared according to Production Example 1 under a reduced pressure of 50 mbar and at a rate of rotation of 0.5 revolutions/min. Impregnation was carried out at room temperature over a period of 4 hours. The vacuum was then broken and the impregnated support was transferred to a belt calciner. The impregnated material was further heated on a belt calciner at a temperature of 290° C. in nitrogen flow according to calcination parameters described in WO 2012/140614 to form an Ag-containing intermediate product.

Step 2. Preparation of Final Catalyst 328 kg of Ag complex solution prepared according to Production Example 1 were mixed with 13.23 kg of promoter solution I containing Li and S, 14.37 kg of promoter solution II containing Cs and W, and 24.93 kg of promoter solution III containing Re to form Ag impregnation solution.

The promoter solution I was prepared by dissolving LiNO$_3$ and (NH$_4$)$_2$SO$_4$ in water to form a solution with Li-content of 2.85 wt % and S-content of 0.21 wt %. The promoter solution II was prepared by dissolving CsOH and H$_2$WO$_4$ in water to form a solution with Cs-content of 5.3 wt % and W-content of 3.0 wt %. The promoter solution III was prepared by dissolving NH$_4$ReO$_4$ in water to form a solution with Re-content of 3.7 wt %.

634 kg of Ag-containing intermediate prepared according to Step 1 were impregnated with 357 kg of the Ag impregnation solution under a reduced pressure of 50 mbar and at a rate of rotation of 0.5 revolutions/min. Impregnation was carried out at room temperature over a period of 3 hours. The vacuum was then broken and the impregnated support was transferred to a belt calciner. The impregnated material was further heated on a belt calciner at a temperature of 290° C. in nitrogen flow according to calcination parameters described in WO 2012/140614 to form a final ethylene oxide catalyst.

The invention claimed is:

1. A method for preparing a silver impregnation solution comprising:
   (a) charging a neutralization reactor R1 with an aqueous organic amine;
   (b) adding oxalic acid powder through a first feeding conduit to the neutralization reactor R1 to obtain an aqueous oxalic acid-organic amine solution;
   (c) directing the aqueous oxalic acid-organic amine solution from the neutralization reactor to a complexation reactor R2;
   (d) adding particulate silver oxide, calculated as Ag metal through a second feeding conduit to the complexation reactor R2 to obtain a silver impregnation solution; and, optionally, (e) subjecting the silver impregnation solution to filtration;

wherein the molar ratio of oxalic acid to silver is 0.505 to 0.65.

2. The method of claim 1, wherein the oxalic acid to silver molar ratio is in the range of 0.505 to 0.6.

3. The method of claim 1, wherein, prior to step (b), the aqueous organic amine is adjusted to a temperature $T_1$, wherein $$T_1 \leq 100° \text{ C.} - \Delta T_{AD\text{-}1}$$

wherein $\Delta T_{AD\text{-}1}$ is the maximum adiabatic temperature rise during step (b).

4. The method of claim 1, wherein prior to step (d), the aqueous oxalic acid-organic amine solution is adjusted to a temperature T2, wherein $$T_2 \leq 80° \text{ C.} - \Delta T_{AD\text{-}2}$$

wherein $\Delta T_{AD\text{-}2}$ is the maximum adiabatic temperature rise during step (d).

5. The method of claim 1, wherein the oxalic acid is oxalic acid dihydrate containing 1500 ppmw or less, of sulfate anions.

6. The method of claim 1, wherein the oxalic acid is oxalic acid dihydrate powder having a primary particle size distribution such that at least 75% by volume of the particles have a particle size of 250 μm or lower.

7. The method of claim 1, wherein the time period of step (d) does not exceed 3 minutes per kg of added silver oxide, calculated as Ag metal.

8. The method of claim 1, wherein the silver oxide has a water content of up to 20% by weight.

9. The method of claim 1, wherein the silver oxide has a primary particle size distribution such that at least 75% by volume of the particles have a particle size of 250 μm or lower.

10. The method of claim 1, wherein the silver oxide has a primary particle size distribution such that at least 75% by volume of the particles have a particle size of 50 μm or lower, and an agglomerated particle size distribution such that at least 30% by volume is in the form of aggregates having an apparent particle size of at least 50 μm.

11. The method of claim 1, wherein the silver oxide has a specific surface area of 0.1 m²/g to 10 m²/g.

12. The method of claim 1, wherein the silver oxide contains at most 500 ppmw of trace metals selected from copper, iron, lead, nickel, and sodium.

13. The method of claim 1, wherein the silver oxide contains at most 500 ppmw of the sum of chloride and sulfate anions.

14. The method of claim 1, wherein the final silver impregnation solution contains 24 to 35% by weight of dissolved silver cations.

15. The method of claim 1, wherein the organic amine comprises a vicinal alkylene diamine.

16. The method of claim 1, wherein the molar ratio of amine nitrogen atoms of the organic amine to silver cations is at least 2.66.

17. The method of claim 1, wherein aqueous oxalic acid-organic amine solution is withdrawn from the neutralization reactor and directed alternately into a first complexation reactor $R2_1$; and into a second complexation reactor $R2_2$.

18. A method for producing a catalyst effective in the oxidative conversion of ethylene to ethylene oxide, the method comprising (i) preparing a silver impregnation solution according to the method of claim 1;

(ii) impregnating a refractory support with the silver impregnation solution; and (iii) subjecting the impregnated refractory support to a calcination process.

19. The method of claim 15, wherein the organic amine comprises ethylenediamine.

20. The method of claim 2, wherein the molar ratio of amine nitrogen atoms of the organic amine to silver cations is at least 3.00.

21. The method of claim 1, wherein at least 200 kg of particulate silver oxide, calculated as Ag metal, is added through the second feeding conduit.

22. The method of claim 1, wherein at least 300 kg of particulate silver oxide, calculated as Ag metal, is added through the second feeding conduit.

* * * * *